United States Patent [19]
Moineau et al.

[11] Patent Number: 5,928,688
[45] Date of Patent: Jul. 27, 1999

[54] **DNA ENCODING PHAGE ABORTIVE INFECTION PROTEIN FROM *LACTOCOCCUS LACTIS* AND METHOD OF USE THEREOF**

[75] Inventors: Sylvain Moineau; Barbara J. Holler, both of Rochester, Minn.; Peter A. Vandenbergh, Sarasota, Fla.; Ebenezer R. Vedamuthu; Jeffrey K. Kondo, both of Rochester, Minn.

[73] Assignee: Quest International Flavors & Food Ingredients Company, Bridgewater, N.J.

[21] Appl. No.: 08/909,425

[22] Filed: Aug. 11, 1997

Related U.S. Application Data

[62] Division of application No. 08/565,907, Dec. 1, 1995.
[51] Int. Cl.⁶ .............................. A23C 9/12; C12N 15/31; C12N 1/21; C12N 15/63
[52] U.S. Cl. ..................... 426/43; 435/172.3; 435/252.3; 435/320.1
[58] Field of Search .......................... 426/43; 435/172.3, 435/252.3, 320.1

[56] References Cited

PUBLICATIONS

Garvey, P. et al. "Cloning and DNA sequence analysis of two abortive infection phage resistance determinants from the Lactococcal plasmid pNP40" Applied and Environmental Microbiology (Dec. 1995), vol. 61, No. 12, pp. 4321–4328.
Jarvis, A.W., et al., Intervirology 32:2–9 (1991).
Hill, C., FEMS Microbiol. Rev. 12:87–108 (1993).
Sing, W.D., et al., J. Dairy Sci. 73:2239–2251 (1990).
McLandsborough, L.A., et al., Appl. Environ. Microbiol. 61:2023–2026 (1995).
Molineaux, I.J., New Biol. 3:230–236 (1991).
Snyder, L., Mol. Microbiol. 15:415–420 (1995).
Hill, C., et al., Appl. Environ. Microbiol. 56:2255–2258 (1990).
Cluzel, P. J., et al., Appl. Environ. Microbiol. 57:3547–3551 (1991).
Durmaz, E., et al., J. Bacteriol. 174:7463–7469 (1992).
Anba, J., et al., J. Bacteriol. 177:3818–3823 (1995).
Hill, C., et al., Appl. Environ. Microbiol. 57:283–288 (1991).
Moineau, S., et al., Appl. Environ. Microbiol. 59:208–212 (1993).
Bidnenko, E., et al., J. Bacteriol. 177:3824–3829 (1995).
Sanders, M. E., et al., Appl. Environ. Microbiol. 52:1001–1007 (1986).
Alatossava, T., et al., Appl. Environ. Microbiol. 57:1346–1353 (1991).
Moineau, S., et al., Appl. Environ. Microbiol. 59:197–202 (1993).
Moineau, S., et al., Appl. Environ. Microbiol. 61:2193–2202 (1995).
Moineau, S., et al., Can. J. Microbiol. 38:875–882 (1992).
Moineau, S., et al., Appl. Environ. Microbiol. 60:1832–1841 (1994).
Jarvis, A. W., Appl. Environ. Microbiol. 36:785–789 (1978).
Sanders, M. E., et al., Appl. Environ. Microbiol. 40:500–506 (1980).
Behnke, D., et al., Virology, 85:118–128 (1978).
Moineau, S., et al., Appl. Environ. Microbiol. 59:2034–2040 (1993).
O'Sullivan, D.J., et al., Appl. Environ. Microbiol. 59:2730–2733 (1993).
Gonzalez, C.F., et al., Appl. Environ. Microbiol. 46:81–89 (1983).
Holo, H., et al., Appl. Environ. Microbiol. 55:3119–3123 (1989).
Dinsmore, P.K., et al., Appl. Environ. Microbiol. 60:1129–1136 (1994).
DeVos, W. M., FEMS Microbiol. Rev. 46:281–295 (1987).
Sing, W.D., et al., Appl. Environ. Microbiol. 59:365–372 (1993).
Casey, J., et al., Appl. Environ. Microbiol. 58:3283–3291 (1992).
Durmaz, E., et al., Appl. Environ. Microbiol. 61:1266–1273 (1995).
O'Sullivan, D. J., et al., J. Bacteriol. 177:134–143 (1995).
Terzaghi, G. E., et al., Appl. Environ. Microbiol. 29:807–813 (1975).

*Primary Examiner*—Kawai Lau
*Attorney, Agent, or Firm*—Ian C. McLeod

[57] ABSTRACT

DNA encoding phage resistance protein which aborts infection by the phage, designated as AbiE. The DNA which is contained in a *Lactococcus lactis* deposited as NRRL-B-21443 and described in SEQ ID NO:1, is incorporated into a bacterium to encode the AbiE and provide phage resistance. Lactococcus and other bacteria encoding the AbiE are useful in industrial fermentations wherein phage are a problem.

12 Claims, 8 Drawing Sheets

```
       EcoRI
   1   GAATTCATGTTTGTTGGATGAGCCATGCATGATAAAGCATTAAATCTTGTTGGACAGGTTTTAAATATA
  71   ACGTATTCCCTTACCTGTTTTGTTTTAATTTCATGACGTCACTCACTCAAGTAATAAATGCAGTTTGTTTGACTGTTCCATCAAGATTAAA
 141   GACATCTGTTTTTTTTAATTTCATGACGTCACTCACTCAAGTAATAAATGCAGTTTGTTTGACTGTTCCATCAAGATTAAA
 211   GTATAGTTACGACGACCAGCACGACGAAAACTATCAAGTAGTGTATCCTGCACCATTTTAAGATATTGAAT
 281   CTTTAATCGGTAAAACAAGTTGTTGCACCATGATACTATTGCTCCTTAAAATCAATTAATTGCTTTATG
 351   ATAGCAAATACGCTATCATAATAGTATGGAAAAATTTGAGTTTGATTATTACGATTGGGCTGAATTTGAA
 421   CAGTTCTTAGATCAGTTACCTGATAAAGATGCTGCTAAGTAATTGCAACCATTCAAAATATTGAAAATA
 491   ATGGCCCTCTTAGTCGCTGAAAGACAATTATGGGTCAAAAAACTAGAAAATAATCTTTATGAAATTCGTC
 561   TAAGCGAGCTTCAAACATCCAAAGAGCGATTTATTTAAAGTCAAAGTAGTCAATACATTATTACTAAT
 631   GCGTTCACGAAAAAAACGCAAAAACCTGAAAATCAAAAGGAAATTGCTCGGAATAGACGCAGTCAGT
 701   ATTTGAATAAGGAGGAAAACCAATGAGTAAACTTGATGCATATGTTGCTGAACGTAGTAAAAAATCCC
 771   AAATTTCACACAATTGTTGAGCAAGAAAATATTAATTTAGAGGTGGCAGTAAAAGTCCATGACCTGCGTG
 841   AAAATATGGGGTTAAGTCAACGTGAATTGCTACTCTGATTGGTAAACCACATCAACCATCGCACGCAT
 911   TGAAAATGGTTCGATGAATGCTTCAACAAAAATGTTATCAGAAGTGCCCAAGCTACTAATCAACGATTA
 981   ACTATTCAATTAATTCTACATTTTAAGATCTATTATATCATTAACAAAAAAATAGCCCCTAATAAACC
1051   AAAGTAATTTATTAGGGCTATTTATTTAAAGTTTTTAAAGGGTTATTTCTAATTATAGTCCCTTAATT
1121   TCCATTTCGTGTCTAATTATTTGACATTAGTCCATACAATAGTGACTCTAAGATTTAAGGATAACATCA
1191   ACTTTCAACATAAGCACAATAACTATTTTTTATTATAATTGAAAAGAGAATTGAATTATTACCTATAAA
1261   ACTTAAAGGAGTATAATTATGAAAAAAGAGTTACTGAATTATATGATTTTATATTTGATCCTATTTTTC
              M  K  K  E  F  T  E  L  Y  D  F  F  F  D  P  I  F  L
1331   TTGTAAGATACGGCTATTATGGATAGATCTATTAAAACCAAAAAATGAATCCTCCAAAAGTTGAATTAGA
        V  R  Y  G  Y  Y  D  R  S  I  K  T  K  K  M  N  P  P  K  V  E  L  D
1401   CAATGAATATGGAAAATCAGATTCTTTTTATTTTAAAGTATTTAATATGGAATCCTTTGCAGATTATTA
        N  E  Y  G  K  S  D  S  F  Y  F  K  V  F  N  M  E  S  F  A  D  Y  L
```

FIG. 4A

```
1471  AGGAGTCATGATTAAAAACACATTTAACGGTAAAAAAACCTCTATCAACAGACCCAGTATATTTAATA
       R  S  H  D  L  K  T  H  F  N  G  K  K  P  L  S  T  D  P  V  Y  F  N  I

1541  TTCCAAAAATATAGAAGCTAGAAGACAATATAAGATGCCCAATTTATACAGTTATATGGCATTAAATTA
       P  K  N  I  E  A  R  R  Q  Y  K  M  P  N  L  Y  S  Y  M  A  L  N  Y

1611  TTATATATGTGACAATAAAAAGAGAGTTTATAGAAGTATTTATTGATAACAAATTTTCAACGTCAAAATT
       Y  I  C  D  N  K  K  E  F  I  E  V  F  I  D  N  K  F  S  T  S  K  F

1681  TTTAATCAATTGAATTTGATTATCCTAAGACACAAGAAATTACACAACAAACATTATATGGAGGAATAA
       F  N  Q  L  N  F  D  Y  P  K  T  Q  E  I  T  Q  T  L  L  Y  G  G  I  K
                                                                    NcoI
1751  AGAAATTACATTTAGATTTATCTAATTTTTATCATACTTTATATACACATAGTATACCATGATGATTGA
       K  L  H  L  D  L  S  N  F  Y  H  T  L  Y  T  H  S  I  P  W  M  I  D

1821  TGGAAAATCTGCATCTAAACAAAATAGAAAAAAAGGGTTTCTAATACATTAGATACTTTGATTACAGCT
       G  K  S  A  S  K  Q  N  R  K  K  G  F  S  N  T  L  D  T  L  I  T  A

1891  TGTCAATACGACGAAACATGGCATTCCAACTGGAAATCTATTGTCTAGGATTATTACCGAACTATATA
       C  Q  Y  D  E  T  H  G  I  P  T  G  N  L  L  S  R  I  I  T  E  L  Y  M

1961  TGTGCCATTTGATAAACAATGAAATATAAAGAAGTTTGTGTATTCAAGATATGTGAGATGATTTATATT
       C  H  F  D  K  Q  M  E  Y  K  K  F  V  Y  S  R  Y  V  D  D  F  I  F

2031  TCCGTTTACTTTTGAGAATGAAAAGCAAGAATTTTAAAATGAATTAATCTAATCTGTCGAGAAATAAC
       P  F  T  F  E  N  E  K  Q  E  F  L  N  E  F  N  L  I  C  R  E  N  N

2101  TTAATTATTAATGATAATAAAACGAAAGTTGACAATTTCCCGTTTGTTGATAAATCGAGTAAATCGGATA
       L  I  I  N  D  N  K  T  K  V  D  N  F  P  F  V  D  K  S  S  K  S  D  I

2171  TTTTTCTTTTTTGAAAATATTACTTCAACTAATTCCAACGACAAGTGGATTAAAGAATAAGCAATTT
       F  S  F  F  E  N  I  T  S  T  N  S  N  D  K  W  I  K  E  I  S  N  F
```

FIG. 4B

```
2241  TATAGATTATTGTGTGAATGAAGAACATTAGGAATAAGGGAGCTATAAAATGTATTTCCCAGTTATA
       I  D  Y  C  V  N  E  E  H  L  G  N  K  G  A  I  K  C  I  F  P  V  I

2311  ACAAATACATTGAAACAACAAAAAAAGTAGATACTAAAAATATAGACAATATCTTTCGAAAGAAACATGG
       T  N  T  L  K  Q  Q  K  K  V  D  T  K  N  I  D  N  I  F  S  K  R  N  M  V

2381  TTACCAATTTTAATGTTTTCGAAAAAATATTAGATTTATCATTAAAGATTCAAGATTAACTAATAAGTT
       T  N  F  N  V  F  E  K  I  L  D  L  S  L  K  D  S  R  L  T  N  K  F

2451  TTTGACTTTCTCTTTGAAAATATTAATGAATTTGGATTTTCAAGTTTATCAGTTTCAAATATTGTAAAAAA
       L  T  F  F  E  N  I  N  E  F  G  F  S  S  L  S  A  S  N  I  V  K  K

2521  TATTTTAGTAATAATTCAAGGGCTTAAAGAAAAATAGACCACTATCGTAAAAAATAATTTAATCAAG
       Y  F  S  N  N  S  K  G  L  K  E  K  I  D  H  Y  R  K  N  N  F  N  Q  E

2591  AATTATATCAAATATTGTGTATATGGTTGTCTTTGAAATAGATGATTTATTAAATCAAGAAGAATTACT
       L  Y  Q  I  L  L  Y  M  V  V  F  E  I  D  D  L  L  N  Q  E  E  L  L

2661  AAACTTAATTGATTAAATATTGATGATTATCTTTAATTTAGGACGATTTTATACCTAAAGAATAGT
       N  L  I  D  L  N  I  D  D  Y  S  L  I  L  G  T  I  L  Y  L  K  N  S

2731  TCATATAAATTGGAAAAATTATTAAAAAAATAGATCAATTATTATTAATACTTCATGCCAACTACGACG
       S  Y  K  L  E  K  L  L  K  K  I  D  Q  L  F  I  N  T  H  A  N  Y  D  V

2801  TTAAAACTTCTCGTATGGCAGAAAAATTATGGCTATTTCGTTATTCTTTATTTTTAAATTGTAAGAA
       K  T  S  R  M  A  E  K  L  W  L  F  R  Y  F  F  F  F  L  N  C  K  N

EcoRV
2871  TATTTTTAGTCAAAAGAGATAAATAGTTATTGTCAATCTCAAAACTATAATTCAGGACAGAACGGATAT
       I  F  S  Q  K  E  I  N  S  Y  C  Q  S  Q  N  Y  N  S  G  Q  N  G  Y

2941  CAAACAGAACTTAATTGGAATTATATTAAAGGTCAAGGGAAGGATCTTAGAGCGAATAACTTTTTTAATG
       Q  T  E  L  N  W  N  Y  I  K  G  Q  G  K  D  L  R  A  N  N  F  F  N  E
```

FIG. 4C

```
3011  AATTGATAGTAAAGAAGTTGGTTAATTCTTGTGTGAGAACGAAGATTCAAATATTTAAATTGATA
       L  I  V  K  E  V  W  L  I  S  C  G  E  N  E  D  F  K  Y  L  N  *
3081  AGTATTTGAAATCTATTATTAGTTCCTGAAAAAATAGCTGTGTCTGTGTCAATATAAATGACAAGACACAG
3151  CTATTTTTTAATTTGAAATTTATAATTTAAATGAACATTTTTGTAAGAAACCTTTTTTCTGTTCT
3221  TTCAATAAATCTAATTTCCGCTGATGAAGAGCGATAGTGTCATCTAGCTGTTTAAAGAATGAACCTATTT
3291  TTTGTTGCTCTGAATTATTCTGAGGAATCGATAGCTTCAGTTCAGTCAACATGTCCATAACAATGTACGG
3361  AATATTTCCTGTACGAGCTTCCTGTTTTATTTTTTAGGCAGCTTATTTCCAATTCTGAAAATATAAAA
3431  CTTCTATCTACTAGAAACTCTTGGAGCACATAAGTTCGTTGATAGGCATTGAACTTATTATCCGGCTAAA
3501  TGCATGTATCCAACTGTGCTCCATTACCTGCCAATTGTAATGGACGGTCCTTCAAACGCTGCTACATCGA
3571  TCCTATATTTTTAATTCCAGAAGTATAAAAATCATACTTGCCATTTCAACCATTGCCATTGCATCTAA
3641  TTTTCCGGTGCTTATTTAGTAATAATCTCCTAACTACGCTTCCCAATCGTCAGCAACCCCGCAAAT
3711  CGCAATTCAGGAACTTTAGCCCCATTTTAGGGAACATTTTTGTAAGAACCTTTTTTCTGTTCCTTGA
3781  GCAAATCTAACTTACGCTGATGAAGAGCGATAGTGTTATCCAGCTGCTTGAAGAATAATACTTTCAAATGTT
3851  TTGTTCCTCAATTGCAGGGACACTTAGTCCAATATCTTTAATATCAGTAGATCTTATTCAAGATTTTGAAATATAAATTCAT
3921  GATCCAGTGCTATATCTAGTGCAACAATACCCGTCGGACTTCATTTTACCAAGAGTCGTTTTACCAATATCTCCAACCGG
3991  TACCTTTATGGCAGCAACACCTCGACCAATAACAACGTCGTGTTTAGTAACTTGAGTTGTCCATACTCTCGGT
4061  TGCTCGGACACTTAGAATGAGATCATCTTTTCAGCTTGTTTAGTAATCATTAGAGTCATCAGTATAAT
4131  AAAACACGACCATTTTCATGTCAGCATTACCTTGCACAAGAATATAATCATTAGAGATCATCAGTATAAT
4201  TTTCTGAATTAGGAGACTGTCCCATCACTATTCGAACTTCGTCTCCCAACTTACGCAGTTCCCATTCATC
4271  CGTGAATCCTTTAAATGCAATTCTGGAACTTCTTTTTAACTGAATCATCTATTTTCGCCATAGTCCCC
4341  ACCATTTTCTTGGTTTTTTCTTGGTCTTGTCTTTCCTATCCTTTTTTTGATCTTTGATTGTTCCTGCAAATTTCCAA
4411  CTTCTCTTTAAGAGCGTTCACTTCATCTTTATATTGATTGTCTAAGTGTTTGAATTC
                                                    EcoRI
```

FIG. 4D

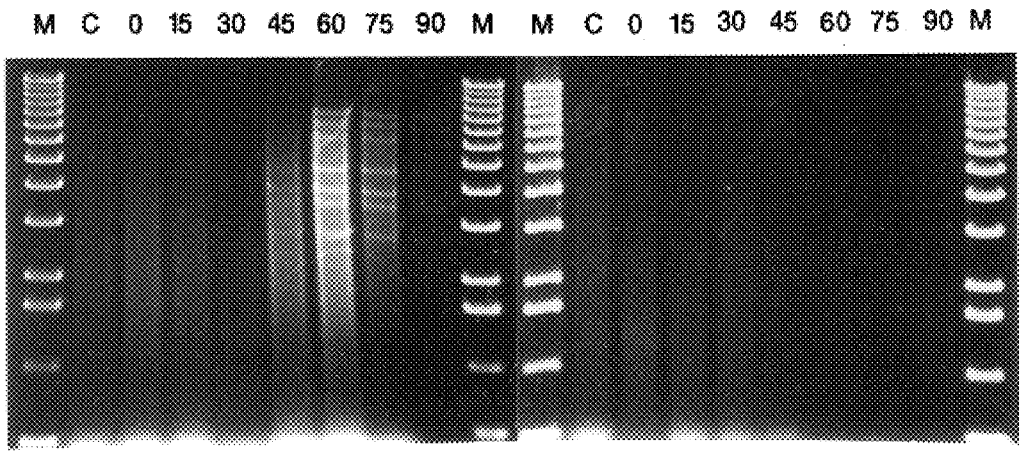
FIG. 5A  FIG. 5B
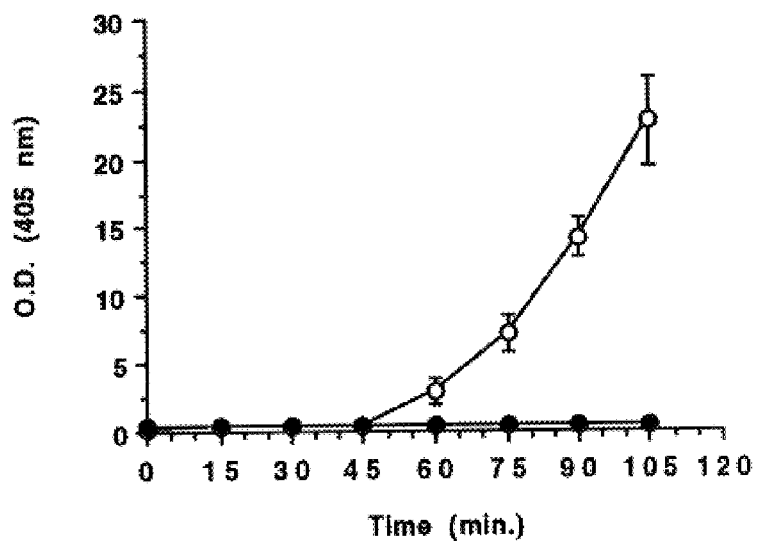
FIG. 5C
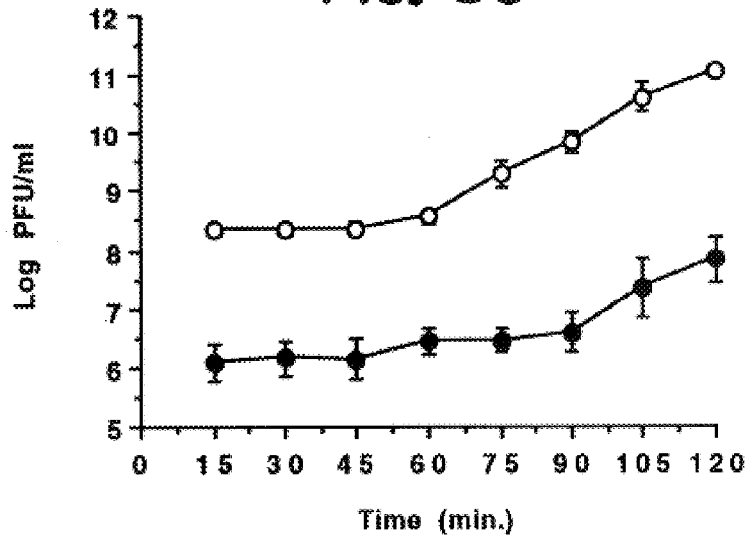
FIG. 5D

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 4467
      (B) TYPE: Nucleotide
      (C) STRANDEDNESS: Single
      (D) TOPOLOGY: Linear (ii) MOLECULE TYPE:
      (A) DESCRIPTION: Genomic DNA (iii) HYPOTHETICAL: No (iv) ANTI-SENSE: No -continued (v) FRAGMENT TYPE: N/A (vi) ORIGINAL SOURCE:
    (A) ORGANISM: Lactococcus lactis
    (B) STRAIN:
    (C) INDIVIDUAL ISOLATE: W1
    (D) DEVELOPMENTAL STAGE: N/A
    (E) HAPLOTYPE: N/A
    (F) TISSUE TYPE: N/A
    (G) CELL TYPE: bacterium
    (H) CELL LINE: N/A
    (I) ORGANELLE: N/A (vii) IMMEDIATE SOURCE:
    (A) LIBRARY: genomic
    (B) CLONE: SMQ-20

(viii) POSITION IN GENOME: N/A (ix) FEATURE:
    (A) NAME/KEY: phage abortive infection
    (B) LOCATION: N/A
    (C) IDENTIFICATION METHOD: sequencing
    (D) OTHER INFORMATION: DNA encoding phage resistance (x) PUBLICATION INFORMATION: N/A (xi) SEQUENCE DESCRIPTION: SEQ ID NO: 1:

```
GAATTCATGT TTTGTTGGAT GAGCCATGCA TGATAAAGCA TTAAATCTTG TTGGACAGGT       60

TTTAAATATA ACGTATTTCC CTTACCTGTT TTTTGATCAT GAATAAATGC AGTTTGTTTG      120

ACTGTTCCAT CAAGATTAAA GACATCTGTT TTTTTTAATT TCATGACGTC ACTCACACGT      180

AGCAAGGTCG CTTTCCCAAC TTGGAAAATT GTATAGTTAC GACGACCAGC ACGAAAACTA      240

TCAAGTAGTG TATCCTGCAC CATTTTTAAG ATATTTGAAT CTTTAATCGG TAAAACAAGT      300

TGTTGCACCA TGATACTATT GCTCCTTTAA AATCAATTAA TTGCTTTATG ATAGCAAATA      360

CGCTATCATA ATAGTATGGA AAAATTTGAG TTTGATTATT ACGATTGGGC TGAATTTGAA      420

CAGTTCTTAG ATCAGTTACC TGATAAAGAT GCTGCTAAGT TAATTGCAAC CATTCAAAAT      480

ATTGAAAATA ATGGCCTCTT AGTCGCTGAA AGACAATTAT GGGTCAAAAA ACTAGAAAAT      540

AATCTTTATG AAATTCGTTC TAAGCGAGCT TCAAACATCC AAAGAGCGAT TTATTTTAAA      600

GTCAAAGGTA GTCAATACAT TATTACTAAT GCGTTCACGA AAAAAACGCA AAAGACACCT      660

GAAAATCAAA AGGAAATTGC TCGGAATAGA CGCAGTCAGT ATTTGAATAA GGAGGAAAAC      720

CAATGAGTAA ACTTGATGCA TATGTTGCTG AACGTAGTAA AAAAAATCCC AAATTTTCAC      780

AAATTGTTGA GCAAGAAAAT ATTAATTTAG AGGTGGCAGT AAAAGTCCAT GACCTGCGTG      840

AAAATATGGG GTTAAGTCAA CGTGAATTTG CTACTCTGAT TGGTAAACCA CAATCAACCA      900

TCGCACGCAT TGAAAATGGT TCGATGAATG CTTCAACAAA AATGTTATCA GAGATTGCCC      960

AAGCTACTAA TCAACGATTA ACTATTCAAT TTAATTCTAC ATTTTAAGAT CTATTATATC     1020

ATTTAACAAA AAAATAGCCC CTAATAAACC AAAGTAATTT ATTAGGGGCT ATTTAATAG     1080

TTTTTTAAAG GGGTTATTTT CTAATTATAG TCCCTTAATT TCCATTTTCG TGTCTAATTA     1140

TTTGACATTA GTCCATACAA TAGTGACTCT AAGATTTAAG GATAACATCA ACTTTCAACA     1200

TAAGCACAAT AACTATTTTT TTATTATAAT TGAAAAGAGA ATTGAATTAT TACCTATAAA     1260

ACTTAAAGGA GTATAATT ATG AAA AAA GAG TTT ACT GAA TTA TAT GAT         1308
                   Met Lys Lys Glu Phe Thr Glu Leu Tyr Asp
                                 5                       10

TTT ATA TTT GAT CCT ATT TTT CTT GTA AGA TAC GGC TAT TAT GAT          1353
Phe Ile Phe Asp Pro Ile Phe Leu Val Arg Tyr Gly Tyr Tyr Asp
               15                  20                  25

AGA TCT ATT AAA ACC AAA AAA ATG AAT CCT CCA AAA GTT GAA TTA          1398
```

-continued

| | | |
|---|---|---|
| Arg Ser Ile Lys Thr Lys Lys Met Asn Pro Lys Val Glu Leu<br>30              35              40 | | |
| GAC AAT GAA TAT GGA AAA TCA GAT TCT TTT TAT TTT AAA GTA TTT<br>Asp Asn Glu Tyr Gly Lys Ser Asp Ser Phe Tyr Phe Lys Val Phe<br>45              50              55 | 1443 | |
| AAT ATG GAA TCC TTT GCA GAT TAT TTA AGG AGT CAT GAT TTA AAA<br>Asn Met Glu Ser Phe Ala Asp Tyr Leu Arg Ser His Asp Leu Lys<br>60              65              70 | 1488 | |
| ACA CAT TTT AAC GGT AAA AAA CCT CTA TCA ACA GAC CCA GTA TAT<br>Thr His Phe Asn Gly Lys Lys Pro Leu Ser Thr Asp Pro Val Tyr<br>75              80              85 | 1533 | |
| TTT AAT ATT CCA AAA AAT ATA GAA GCT AGA AGA CAA TAT AAG ATG<br>Phe Asn Ile Pro Lys Asn Ile Glu Ala Arg Arg Gln Tyr Lys Met<br>90              95              100 | 1578 | |
| CCC AAT TTA TAC AGT TAT ATG GCA TTA AAT TAT TAT ATA TGT GAC<br>Pro Asn Leu Tyr Ser Tyr Met Ala Leu Asn Tyr Tyr Ile Cys Asp<br>105             110             115 | 1623 | |
| AAT AAA AAA GAG TTT ATA GAA GTA TTT ATT GAT AAC AAA TTT TCA<br>Asn Lys Lys Glu Phe Ile Glu Vla Phe Ile Asp Asn Lys Phe Ser<br>120             125             130 | 1668 | |
| ACG TCA AAA TTT TTT AAT CAA TTG AAT TTT GAT TAT CCT AAG ACA<br>Thr Ser Lys Phe Phe Asn Gln Leu Asn Phe Asp Tyr Pro Lys Thr<br>135             140             145 | 1713 | |
| CAA GAA ATT ACA CAA ACA TTA TTA TAT GGA GGA ATA AAG AAA TTA<br>Gln Glu Ile Thr Gln Thr Leu Leu Tyr Gly Gly Ile Lys Lys Leu<br>150             155             160 | 1758 | |
| CAT TTA GAT TTA TCT AAT TTT TAT CAT ACT TTA TAT ACA CAT AGT<br>His Leu Asp Leu Ser Asn Phe Tyr His Thr Leu Tyr Thr His Ser<br>165             170             175 | 1803 | |
| ATA CCA TGG ATG ATT GAT GGA AAA TCT GCA TCT AAA CAA AAT AGA<br>Ile Pro Trp Met Ile Asp Gly Lys Ser Ala Ser Lys Gln Asn Arg<br>180             185             190 | 1848 | |
| AAA AAA GGG TTT TCT AAT ACA TTA GAT ACT TTG ATT ACA GCT TGT<br>Lys Lys Gly Phe Ser Asn Thr Leu Asp Thr Leu Ile Thr Ala Cys<br>195             200             205 | 1893 | |
| CAA TAC GAC GAA ACA CAT GGC ATT CCA ACT GGA AAT CTA TTG TCT<br>Gln Tyr Asp Glu Thr His Gly Ile Pro Thr Gly Asn Leu Leu Ser<br>210             215             220 | 1938 | |
| AGG ATT ATT ACC GAA CTA TAT ATG TGC CAT TTT GAT AAA CAA ATG<br>Arg Ile Ile Thr Glu Leu Tyr Met Cys His Phe Asp Lys Gln Met<br>225             230             235 | 1983 | |
| GAA TAT AAG AAG TTT GTG TAT TCA AGA TAT GTA GAT GAT TTT ATA<br>Glu Tyr Lys Lys Phe Val Tyr Ser Arg Tyr Val Asp Asp Phe Ile<br>240             245             250 | 2028 | |
| TTT CCG TTT ACT TTT GAG AAT GAA AAG CAA GAA TTT TTA AAT GAA<br>Phe Pro Phe Thr Phe Glu Asn Glu Lys Gln Glu Phe Leu Asn Glu<br>255             260             265 | 2073 | |
| TTT AAT CTA ATC TGT CGA GAA AAT AAC TTA ATT ATT AAT GAT AAT<br>Phe Asn Leu Ile Cys Arg Glu Asn Asn Leu Ile Ile Asn Asp Asn<br>270             275             280 | 2118 | |
| AAA ACG AAA GTT GAC AAT TTC CCG TTT GTT GAT AAA TCG AGT AAA<br>Lys Thr Lys Val Asp Asn Phe Pro Phe Val Asp Lys Ser Ser Lys<br>285             290             295 | 2163 | |
| TCG GAT ATT TTT TCT TTT TTT GAA AAT ATT ACT TCA ACT AAT TCC<br>Ser Asp Ile Phe Ser Phe Phe Glu Asn Ile Thr Ser Thr Asn Ser<br>300             305             310 | 2208 | |
| AAC GAC AAG TGG ATT AAA GAA ATA AGC AAT TTT ATA GAT TAT TGT<br>Asn Asp Lys Trp Ile Lys Glu Ile Ser Asn Phe Ile Asp Tyr Cys<br>315             320             325 | 2253 | |
| GTG AAT GAA GAA CAT TTA GGG AAT AAG GGA GCT ATA AAA TGT ATT | 2298 | |

```
Val Asn Glu Glu His Leu Gly Asn Lys Gly Ala Ile Lys Cys Ile
            330                 335                 340

TTC CCA GTT ATA ACA AAT ACA TTG AAA CAA AAA AAA GTA GAT ACT       2343
Phe Pro Val Ile Thr Asn Thr Leu Lys Gln Lys Lys Val Asp Thr
            345                 350                 355

AAA AAT ATA GAC AAT ATC TTT TCG AAA AGA AAC ATG GTT ACC AAT       2388
Lys Asn Ile Asp Asn Ile Phe Ser Lys Arg Asn Met Val Thr Asn
            360                 365                 370

TTT AAT GTT TTC GAA AAA ATA TTA GAT TTA TCA TTA AAA GAT TCA       2433
Phe Asn Val Phe Glu Lys Ile Leu Asp Leu Ser Leu Lys Asp Ser
            375                 380                 385

AGA TTA ACT AAT AAG TTT TTG ACT TTC TTT GAA AAT ATT AAT GAA       2478
Arg Leu Thr Asn Lys Phe Leu Thr Phe Phe Glu Asn Ile Asn Glu
            390                 395                 400

TTT GGA TTT TCA AGT TTA TCA GCT TCA AAT ATT GTA AAA AAA TAT       2523
Phe Gly Phe Ser Ser Leu Ser Ala Ser Asn Ile Val Lys Lys Tyr
            405                 410                 415

TTT AGT AAT AAT TCA AAG GGC TTA AAA GAA AAA ATA GAC CAC TAT       2568
Phe Ser Asn Asn Ser Lys Gly Leu Lys Glu Lys Ile Asp His Tyr
            420                 425                 430

CGT AAA AAT AAT TTT AAT CAA GAA TTA TAT CAA ATA TTG TTG TAT       2613
Arg Lys Asn Asn Phe Asn Gln Glu Leu Tyr Gln Ile Leu Leu Tyr
            435                 440                 445

ATG GTT GTC TTT GAA ATA GAT GAT TTA TTA AAT CAA GAA GAA TTA       2658
Met Val Val Phe Glu Ile Asp Asp Leu Leu Asn Gln Glu Glu Leu
            450                 455                 460

CTA AAC TTA ATT GAT TTA AAT ATT GAT GAT TAT TCT TTA ATT TTA       2703
Leu Asn Leu Ile Asp Leu Asn Ile Asp Asp Tyr Ser Leu Ile Leu
            465                 470                 475

GGG ACG ATT TTA TAC CTA AAG AAT AGT TCA TAT AAA TTG GAA AAA       2748
Gly Thr Ile Leu Tyr Leu Lys Asn Ser Ser Tyr Lys Leu Glu Lys
            480                 485                 490

TTA TTA AAA AAA ATA GAT CAA TTA TTT ATT AAT ACT CAT GCC AAC       2793
Leu Leu Lys Lys Ile Asp Gln Leu Phe Ile Asn Thr His Ala Asn
            495                 500                 505

TAC GAC TTG AAA ACT TCT CGT ATG GCA GAA AAA TTA TGG CTA TTT       2838
Tyr Asp Val Lys Thr Ser Arg Met Ala Glu Lys Leu Trp Leu Phe
            510                 515                 520

CGT TAT TTC TTT TAT TTT TTA AAT TGT AAG AAT ATT TTT AGT CAA       2883
Arg Tyr Phe Phe Tyr Phe Leu Asn Cys Lys Asn Ile Phe Ser Gln
            525                 530                 535

AAA GAG ATA AAT AGT TAT TGT CAA TCT CAA AAC TAT AAT TCA GGA       2928
Lys Glu Ile Asn Ser Tyr Cys Gln Ser Gln Asn Tyr Asn Ser Gly
            540                 545                 550

CAG AAC GGA TAT CAA ACA GAA CTT AAT TGG AAT TAT ATT AAA GGT       2973
Gln Asn Gly Tyr Gln Thr Glu Leu Asn Trp Asn Tyr Ile Lys Gly
            555                 560                 565

CAA GGG AAG GAT CTT AGA GCG AAT AAC TTT TTT AAT GAA TTG ATA       3018
Gln Gly Lys Asp Leu Arg Ala Asn Asn Phe Phe Asn Glu Leu Ile
            570                 575                 580

GTA AAA GAA GTT TGG TTA ATT TCT TGT GGT GAG AAC GAA GAT TTC       3063
Val Lys Glu Val Trp Leu Ile Ser Cys Gly Glu Asn Glu Asp Phe
            585                 590                 595

AAA TAT TTA AAT TGA TA AGTATTTGAA ATCTATTATT AGTTCCTGAA AAAATAGCTG 3120
Lys Tyr Leu Asn

TGTCTTGTCA ATATAAATGA CAAGACACAG CTATTTTTTT TAATTTTGAA ATTTATAATT  3180

TTAAATGAAC ATTTTTTGTA AGAAACCTTT TTTCTGTTCT TTCAATAAAT CTAATTTCCG  3240

CTGATGAAGA GCGATAGTGT CATCTAGCTG TTTAAAGAAT GAACCTATTT TTTGTTGCTC  3300
```

-continued

```
TGAATTATTC TGAGGAATCG ATAGCTTCAG TTCAGTCAAC ATGTCCATAA CAATGTACGG    3360

AATATTTCCT GTACGAGCTT CCTGTTTTAT TTTTTTAGGC AGCTTATTTC CAATTTCTGA    3420

AAATATAAAA CTTCTATCTA CTAGAAACTC TTGGAGCACA TAAGTTCGTT GATAGGCATT    3480

GAACTTATTA TCCGGCTAAA TGCATGTATC CAACTGTTGC TCCATTACCT GCAATTGTAA    3540

TGGACGGTCC TTCAAACGCT GCTACATCGA TCCTATATTT TTTAATTCCA GAAGTATAAA    3600

AATCATACTT GCCATTTTCA ACCATTGCAT TTGCATCTAA TTTTCCGGTG CTTATTTTAG    3660

TAATATCTCC TAACTTACGC TCTTCCCAAT CGTCAGCAAA CCCCGCAAAT CGCAATTCAG    3720

GAACTTTAGC CCCATTTTTA GGGAACATTT TTTGTAAGAA GCCTTTTTTC TGTTCCTTGA    3780

GCAAATCTAA CTTACGCTGA TGAAGAGCGA TAGTGTTATC CAGCTGCTTG AAGAATGAAC    3840

CGATTTTGTC TTGTTCCTCA ATTGCAGGGA CACTTATTAT AGCTTCTTTA ATATCAGTAG    3900

AATTAATACT TTCAAATGTT GATCCAGTGC TATATCTAGT CCAATACCCG TCGGACTTCA    3960

TTTTACCAAG ATTTTGAAAT ATAAATTCAT TACCTTTTAT GGCAGCAACA CCTCGACCAA    4020

TAACAACGTC ATAAGCTGTT TTACCAATAT CTCCAACCGG TGCTCGGACA CTTAGAATGA    4080

GATCATCTTT TTCAGCTTGT TTAGTAACTT GAGTTGTCCA TACTCTCGGT AAAACACGAC    4140

CATTTTTCAT GTCAGCATTA CCTTGCACAA GAATATAATC ATTAGGATCA TCAGTATAAT    4200

TTTCTGAATT AGGAGACTGT CCCATCACTA TTCGAACTTC GTCTCCCAAC TTACGCAGTT    4260

CCCATTCATC CGTGAATCCT TTAAATCGCA ATTCTGGAAC TTTCTTTTTA ACTGAATCAT    4320

CTATTTTCGC CATAGTCCCC ACCATTTTCT TGGTTTTTCT TGTTCTTCTA TCCTTTTTTG    4380

ATCTTTGATT TGTTCCTGCA AATTTTCCAA CTTCTCTTTA AGAGCGTTCA CTTCATCTTT    4440

ATATTGATTG TCTAAGTGTT TGAATTC                                       4467
```

DNA ENCODING PHAGE ABORTIVE INFECTION PROTEIN FROM *LACTOCOCCUS LACTIS* AND METHOD OF USE THEREOF

This is a divisional of copending application Ser. No. 08/565,907 filed on Dec. 1, 1995.

BACKGROUND OF THE INVENTION (1) Field of the Invention

The present invention relates to DNA isolated in a plasmid or in a bacterium encoding a phage resistance protein (designated as AbiE) which aborts infection of the bacterium by the phage. In particular the present invention relates to methods of using the DNA to provide the phage resistance.

(2) Description of Related Art

*Lactococcus lactis* is widely used in mesophilic milk fermentations to produce cheese, buttermilk, cottage cheese and sour cream. Due to the expanding activities in these industries, there is pressure on *L. lactis* starter cultures to perform at industrial standards of consistency and efficiency. Phages are the leading cause of fermentation failures during the manufacture of these cultured dairy products (Jarvis A. W., et al., Intervirology 32:2–9 (1991)). They can ruin a fermentation by inactivating the inoculated, sensitive cultures. Since identification of the causal agent in the mid-30s, the dairy industry has learned to manage with this natural phenomenon by developing various solutions such as better sanitation, process modifications and use of phage-resistant cultures (Hill, C., FEMS Microbiol. Rev. 12:87–108 (1993)).

Extensive studies have been carried out on the innate phage resistance mechanisms of *L. lactis* strains (for review see Hill, C., FEMS Microbiol. Rev. 12:87–108 (1993)). Native barriers against phages have been found and most of them are encoded on plasmids. More than 40 plasmids encoding a variety of phage resistance mechanisms have been identified (Hill, C., FEMS Microbiol. Rev. 12:87–108 (1993)). These anti-phage systems are currently classified in three groups based on their mode of action: blocking of phage adsorption, restriction/modification (R/M), and abortive infection (Abi).

Amongst the natural *L. lactis* phage resistance mechanisms, the Abi systems are believed to be the most powerful due to their overall effects (Sing, W. D., et al., J. Dairy Sci. 73:2239–2251 (1990)). In a classical abortive infection, the phage lytic cycle is inhibited but after adsorption, DNA injection and early phage gene expression. The end result is the typical Abi+ phenotype of reduced burst size and plaque size (McLandsborough, L. A., et al., Appl. Environ. Microbiol. 61:2023–2026 (1995); Molineux, I. J., New Biol. 3:230–236 (1991); Sing, W. D., et al., J. Dairy Sci. 73:2239–2251 (1990); Snyder, L., Mol. Microbiol. 15:415–420 (1995)). Generally, the host is also killed in the abortive process. This suicidal outcome traps the phages within the infected cell and limits their dissemination (Sing, W. D., et al., J. Dairy Sci. 73:2239–2251 (1990)).

Many Abi systems have been identified in other bacterial genera (for review see Molineux, I. J., New Biol. 3:230–236 (1991); and Snyder, L., Mol. Microbiol. 15:415–420 (1995)). Some of these systems have been studied extensively but the molecular basis remains somewhat unclear (Snyder, L., Mol. Microbiol. 15:415–420 (1995)). Recent evidence are now only leading to more specific models for their action (Molineux, I. J., New Biol. 3:230–236 (1991); and Snyder, L., Mol. Microbiol. 15:415–420 (1995)). Likewise, Abi systems are very poorly understood in *L. lactis* (Sing, W. D., et al., J. Dairy Sci. 73:2239–2251 (1990)). To date, five Abi systems have been characterized to molecular level: AbiA (Hill, C., et al., Appl. Environ. Microbiol. 56:2255–2558 (1990), AbiB (Cluzel, P. J., et al., Appl. Environ. Microbiol. 57:3547–3551 (1991), AbiC (Durmaz, E., et al., J. Bacteriol. 174:7463–7469 (1992), AbiD (McLandsborough, L. A., et al., Appl. Environ. Microbiol. 61:2023–2026 (1995) and AbiD1 (Anba, J., et al., J. Bacteriol. 177:3818–3823 (1995). These systems were isolated from different *L. lactis* strains. There is no homology between the Abi proteins except for AbiD and AbiD1 which shared 28% identity (52% similarity). This was the first indication on the existence of a possible family of Abi proteins in *L. lactis* (Anba, J., et al., J. Bacteriol. 177:3818–3823). The absence of homology between the other *L. lactis* Abi mechanisms suggests different mode of action and/or phage targets. Very limited information is available on the molecular mechanisms of *L. lactis* Abi systems. AbiA is believed to somehow interfere with DNA replication of small isometric phages (Hill, C., et al., Appl. Environ. Microbiol. 57:283–288 (1991); and Moineau, S., et al., Appl. Environ. Microbiol. 59:208–212 (1993)). AbiC does not prevent phage DNA replication but reduces the synthesis of structural phage proteins in infected cells (Durmaz, E., et al., J. Bacteriol. 174:7463–7469 (1992); and Moineau, S., et al., Appl. Environ. Microbiol. 59:208–212 (1993)). Recently, Bidnenko et al. (Bidnenko, E., et al., J. Bacteriol. 177:3824–3829 (1995)) reported that AbiD1 interacted with a small isometric phage operon which contained 4 open reading frames (ORFs). It was proposed that AbiD1 and the orf1 gene product interacted to prevent translation of orf3 RNA (Bidnenko, E., et al., J. Bacteriol. 177:3824–3829 (1995)).

Industrial *L. lactis* strains with enhanced phage resistance have been constructed by introducing natural plasmids containing Abi systems into phage-sensitive strains (Sanders, M. E., et al., Appl. Environ. Microbiol. 52:1001–1007 (1986)). These improved strains have already been successfully employed for large scale dairy fermentations. However new phages capable of overcoming the introduced Abi defense system have emerged (Alatossava, T., et al., Appl. Environ. Microbiol. 57:1346–1353 (1991); and Moineau, S., et al., Appl. Environ. Microbiol. 59:197–202 (1993)). Thus, the search for novel phage resistance mechanisms is an ongoing objective for culture suppliers (Moineau, S., et al., Appl. Environ. Microbiol. 61:2193–2202 (1995)).

Lactococcal phages are classified in 12 different species based on morphology and DNA homology (Jarvis, A. W., et al., Intervirology 32:2–9 (1991)). Only three have been studied for genetic details because they are commonly encountered worldwide in dairy plants (Jarvis, A. W., et al., Intervirology 32:2–9 (1991)). Members of the species 936 (small isometric heads), c2 (prolate heads) and P335 (small isometric heads) have been, by far, the most disturbing lactococcal phages (Jarvis, A. W., et al., Intervirology 32:2–9 (1991); and Moineau, S., et al., Can. J. Microbiol. 38:875–882 (1992)). DNA-DNA hybridization studies have revealed the absence of significant DNA homology between the three species (Jarvis, A. W., et al., Intervirology 32:2–9 (1991)). The current consensus is that the 936, P335 and c2 species are genetically distinct and *L. lactis* starter cultures should be resistant against these phages (Moineau, S., et al., Appl. Environ. Microbiol. 61:2193–2202 (1995)).

OBJECTS

It is an object of the present invention to provide DNA encoding a sixth and novel abortive infection mechanism (Abi) from *L. lactis* which acts prior to or at the phage DNA replication and shares no homology with the previously isolated Abi from *L. lactis*. Further, it is an object of the present invention to provide a novel Abi system which is efficient against 936, c2 and P335 phages.

Further, it is an object of the present invention to provide a method and bacteria which prevent phage inactivation of *Lactococcus lactis* strains. Further still, it is an object of the present invention to provide a recombinant bacteria which are economical to prepare and effective in phage inhibition. These and other objects will become increasingly apparent by reference to the following description and the drawings.

BRIEF DESCRIPTION OF DRAWINGS

FIGS. 4A to 4D are a nucleotide sequence of the 4.5-kb EcoRI fragment from pSRQ800 as shown in SEQ ID NO:1. The deduced amino acid sequence of the only significant open reading frame is presented. The putative promoter and RBS are underlined.

FIGS. 5A and 5B are electrophoresis gels showing φul36 DNA replication followed at time intervals during infection of *L. lactis* SMQ-86 (left side) and SMQ-88 (right side). 1-ml samples were taken at time intervals and the total DNA isolated according to the Hill et al. procedure (Hill, C., et al., Appl. Environ. Microbiol. 57:283–288 (1991)). Total DNA was cut with EcoRV and a sample run on a 0.7% agarose gel. Lane M, 1-kb ladder (Gibco/BRL); Lane C, DNA sample prior to phage infection; Lane 0, 15, 30, 45, 65, 75 and 90 indicates time intervals (min.).

FIG. 5C is a graph showing accumulation of the major capsid protein of φuL36 followed at time intervals during infection of *L. lactis* SMQ-86 and SMQ-88 using an ELISA detection system described previously (Moineau, S., et al., Appl. Environ. Microbiol. 59:208–212 (1993)). An O.D. of 0.389±0.132 was obtained at time 105 with infected SMQ-88 cells. Symbols: ○, SMQ-86 (pSA3); ●, SMQ-88 (pSRQ802). Error bar indicates standard deviation for 5 trials. The background level of non-infected cells was 0.296±0.085. Substantial accumulation of protein was produced in φuL36 infected SMQ-86 cells.

FIG. 5D is a graph showing one-step growth curves for φul36 on *L. lactis* SMQ-86 and SMQ-88. The phages were allowed to adsorb to the cells for 5 min., cells were washed twice to remove non-adsorbed phages and then resuspended in LM17 and incubated at 30° C. Time 15 min corresponded to the first phage count after resuspension in LM17. There was much more progeny phage released from SMQ-86.

DESCRIPTION OF PREFERRED EMBODIMENTS

Figure 1:
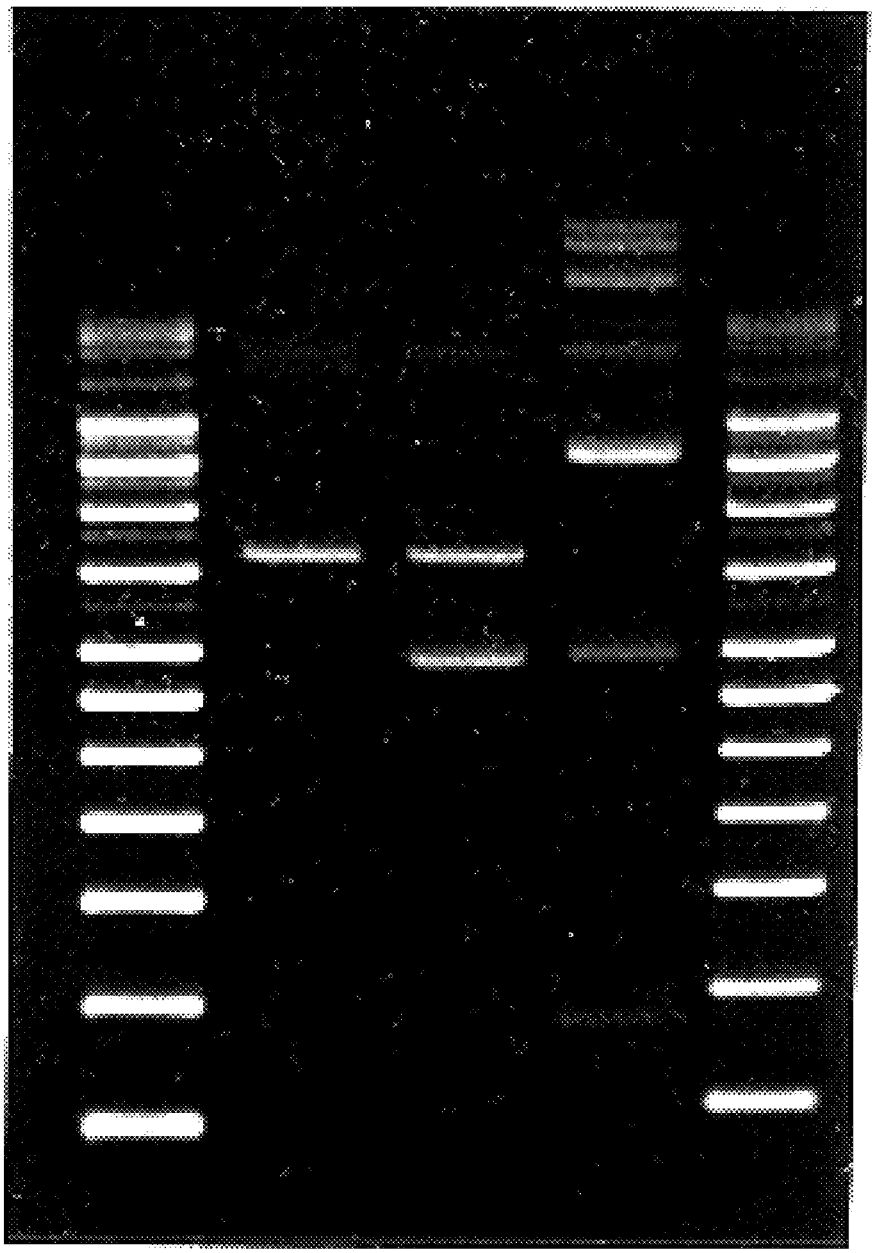
FIG. 1 is a photograph of an electrophoresis gel showing a plasmid analysis of *Lactococcus lactis* strains. Lanes: 1 and 5, supercoiled DNA ladder (Gibco/BRL, Grand Island, N.Y.); 2 *L. lactis* SMQ-16; 3, *L. lactis* SMQ-20; 4, *L. lactis* W-1 (containing plasmid pSRQ800).

The present invention relates to an isolated DNA encoding a protein designated as AbiE which in a *Lactococcus lactis* increases resistance to phages by aborting infection of *Lactococcus lactis* by phages, particularly as contained in *Lactococcus lactis* SMQ20 deposited as NRRL-B-21443 and as set forth in SEQ ID NO:1.

The present invention also relates to a recombinant plasmid containing DNA encoding a protein designated as AbiE which in a *Lactococcus lactis* increases resistance to phages by aborting infection of *Lactococcus lactis* by phages, particularly containing the DNA set forth previously.

The present invention also relates to a bacterium harboring a recombinant plasmid containing DNA encoding a protein designated as AbiE which in a *Lactococcus lactis* increases resistance to phages by aborting infection of *Lactococcus lactis* by phages, particularly a bacterium harboring DNA as set forth previously. The bacterium are preferably Lactococcus, Lactobacillus, Leuconostocs, Pediococcus, Streptococcus thermophilus, Enterococcus, and Bifidobacterium.

The present invention further relates to a method of imparting phage resistance to a bacterium which is phage sensitive which comprises transferring DNA encoding a protein designated as AbiE which increases resistance to phages by aborting infection of *Lactococcus lactis* by phages into the bacterium to impart the phage resistance. Further the present invention relates to a method for fermenting a dairy product, the improvement which comprises using a culture of *Lactococcus lactis* for the fermenting containing transferred DNA encoding a protein designated as AbiE which increases resistance to phages by aborting infection of *Lactococcus lactis* by phages to impart the phage resistance and to produce the dairy product.

Most particularly the present invention relates to *Lactococcus lactis* naturally lacking in phage resistance and containing transferred DNA encoding a protein designated as AbiE which increases resistance to phages by aborting infection of *Lactococcus lactis* by phages, wherein the DNA has a sequence essentially as set forth in SEQ ID NO:1 to impart phage resistance to the *Lactococcus lactis*.

The natural plasmid pSRQ800 was isolated from *Lactococcus lactis* subsp. lactis W1. When introduced into a phage-sensitive *L. lactis* strain, pSRQ800 conferred strong phage resistance against small isometric phages of the 936 and P335 species. It had very limited effect on prolate phages of the c2 species. The phage resistance mechanism encoded on pSRQ800 is a temperature-sensitive abortive infection mechanism (Abi). Plasmid pSRQ800 was mapped and the Abi genetic determinant localized. Cloning and sequencing of the Abi system allowed the identification of a single open reading frame. This ORF coded for a predicted protein of 599 amino acids with an estimated molecular weight of 71.4 kDa and a pI of 8.0. No significant DNA or protein homology was observed with databases. This novel phage resistance mechanism was named AbiE. No phage replication or production of phage major capsid proteins were detected in infected AbiE+ *L. lactis* cells. This system is believed to act at or prior to phage DNA replication. When cloned into a high copy vector, AbiE became effective against the c2 species. Thus when delivered in an appropriate vector, AbiE system was efficient against the three most commonly found lactococcal phage species.

The plasmid pSRQ800 is contained in a deposit of *Lactococcus lactis* SMQ-20 deposited under the Budapest Treaty with the Northern Regional Research Laboratory in Peoria, Ill. on May 17, 1995 as NRRL-B-21443. DNA plasmid pSRQ700 encoding a restriction or modification system (LlaDCHI) is deposited under the Budapest Treaty as NRRL-B-21337 on Sep. 29, 1994 and is used with pSRQ800 to produce a synergistic result. This DNA is described in U.S. application Ser. No. 08/366,480, filed Dec. 30, 1994, which is incorporated by reference herein. The DNA sequence is deposited with GenBank (V16027).

EXAMPLE 1

Materials and Methods

Bacterial Strains, Plasmids, and Media

Strains and plasmids used in this application are listed in Tables 1 and 2. *Escherichia coli* was grown at 37° C. in LB broth. *Lactococcus lactis* strains were grown at 30° C. in M17 (Terzaghi, B. E., et al., Appl. Environ. Microbiol. 29:807–813 (1975)) supplemented with 0.5% glucose (GM17) or 0.5% lactose (LM17). When appropriate, antibiotics were added as follows: for *E. coli*, 50 μg of ampicillin per ml, 10 μg of tetracycline per ml, and 20 μg of chloramphenicol per ml; for *L. lactis*, 5 μg of chloramphenicol per ml, and 5 μg of erythromycin per ml.

Bacteriophage Propagation and Assays

Bacteriophages used in this study are listed in Table 1.

TABLE 1

Bacterial Strains and Bacteriophages used.

| Bacterial strains or and phages | Relevant characteristics[a] | Source[b] |
|---|---|---|
| *Lactococcus lactis* | | |
| LM0230 | Plasmid free, host for 936 and c2 phages; Lac⁻ | |
| UL8 | Multiple plasmids, host for P335 phages; Lac⁺ | |
| W1 | Multiple plasmids including pSRQ800; Lac⁺ | This invention |
| SMQ-16 | LM0230 (pSA3); Lac⁻ Em$^r$ | |
| SMQ-20 | LM0230 (pSA3, pSRQ800); Lac⁻ Em$^r$ Abi⁺ | This invention |
| SMQ-37 | LM0230 (pSRQ801); Lac⁻ Em$^r$ | This invention |
| SMQ-38 | LM0230 (pSRQ802); Lac⁻ Em$^r$ Abi⁺ | This invention |
| SMQ-39 | LM0230 (pSRQ701); Lac⁻ Em$^r$ R⁺/M⁺ | |
| SMQ-52 | LM0230 (pSRQ804); Lac⁻ Em$^r$ | This invention |
| SMQ-54 | LM0230 (pSRQ806); Lac⁻ Em$^r$ | This invention |
| SMQ-57 | LM0230 (pSRQ809); Lac⁻ Em$^r$ | This invention |
| SMQ-86 | UL8 (pSA3); Lac⁺ Em$^r$ | This invention |
| SMQ-88 | UL8 (pSRQ802); Lac⁺ Em$^r$ Abi⁺ | This invention |
| SMQ-130 | LM0230 (pSRQ813); Lac⁻ Cm$^r$ Abi⁺ | This invention |
| SMQ-138 | LM0230 (pSRQ701, pSRQ813); Lac⁻ Em$^r$ Cm$^r$ R⁺/M⁺ Abi⁺ | This invention |
| SMQ-143 | LM0230 (pSRQ815); Lac⁻ Cm$^r$ Abi⁺ | This invention |
| SMQ-251 | LM0230 (pMIG3); Lac⁻ Cm$^r$ | This invention |
| SMQ-252 | LM0230 (pNZ123); Lac⁻ Cm$^r$ | This invention |
| *Escherichia coli* | | |
| DH5α | Transformation host | Gibco/BRL |
| SMQ-92 | DH5α (pSRQ810); Ap$^r$ | This invention |
| SMQ-116 | DH5α (pSRQ812); Ap$^r$ | This invention |
| SMQ-129 | DH5α (pSRQ814); Ap$^r$ | This invention |
| Bacteriophages | | |
| φp2 | Small isometric headed, 936 species, 30.5 kb | L.L. McKay |
| φsk1 | Small isometric headed, 936 species, 28.1 kb | L.L. McKay |
| φjj50 | Small isometric headed, 936 species, 30.5 kb | |
| φc2 | Prolate headed, c2 species, 20.7 kb | |
| φm13 | Prolate headed, c2 species, 20.2 kb | W.E. Sandine |
| φeb1 | Prolate headed, c2 species, 19.6 kb | L.L. McKay |
| φu136 | Small isometric headed, P335 species, 28.8 kb | |
| φQ30 | Small isometric headed, P335 species, 37.0 kb | |
| φQ33 | Small isometric headed, P335 species, 29.6 kb | |

Table 1, Footnotes
[a]Abi⁺, active abortive infection mechanism; Ap$^r$, ampicillin resistance; Cm$^r$, chloramphenicol resistance; Em$^r$, erythromycin resistance; Lac, lactose-fermenting ability; R⁺/M⁺, active restriction/modification enzymes;
[b]L.L. McKay, University of Minnesota, Minneapolis; W.E. Sandine, Oregon State University, Corvallis;

TABLE 2

Plasmids used in this invention.

| Plasmid | Relevant characteristics | Source |
|---|---|---|
| pBS | Cloning vector for sequencing, Ap$^r$, 2.9-kb | Stratagene |
| pMIG3 | Shuttle vector, Cm$^r$, 5.5-kb | |
| pNZ123 | Shuttle vector, Cm$^r$, 2.5-kb | |
| pSA3 | Shuttle vector, Cm$^r$ Tc$^r$ Em$^r$, 10.2-kb | |
| pSR701 | 7.0-kb EcoRI fragment from pSRQ700 cloned into pSA3; Cm$^s$ Tc$^r$ Em$^r$ R⁺/M⁺ | |
| pSRQ800 | Resident plasmid of W1, Abi⁺, 8.0-kb | This Invention |
| pSRQ801 | 3.5-kb EcoRI fragment from pSRQ800 cloned into pSA3; Cm$^s$ Tc$^r$ Em$^r$ | This Invention |

TABLE 2-continued

Plasmids used in this invention.

| Plasmid | Relevant characteristics | Source |
| --- | --- | --- |
| pSRQ802 | 4.5-kb EcoRI fragment from pSRQ800 cloned into pSA3; Cm$^s$ Tc$^r$ Em$^r$ | This invention |
| pSRQ804 | S.7-kb NcoI fragment from pSRQ800 cloned into pSA3; Cm$^s$ Tc$^r$ Em$^r$ | This invention |
| pSRQ806 | 1.8-kb NcoI-EcoRI fragment from pSRQ800 cloned into pSA3; Cm$^s$ Tc$^r$ Em$^r$ | This invention |
| pSRQ809 | 8.0-kb EcoRV fragment from pSRQ800 cloned into pSA3; Cm$^r$ Tc$^s$ Em$^r$ | This invention |
| pSRQ810 | 1.5-kb ECORV-EcoRI from pSRQ800 cloned into pBS; Ap$^r$ | This invention |
| pSRQ812 | 1.2-kb EcORV-ScaI from pSRQ802 cloned into pBS; Ap$^r$ | This invention |
| pSRQ813 | 4.5-kb fragment from pSRQ800 cloned into pMIG3; Cm$^r$ | This invention |
| pSRQ814 | 1.8-kb ECORI-ScaI from pSRQ802 cloned into pBS; Ap$^r$ | This invention |
| pSRQ815 | 4.5-kb EcoRI fragment from pSRQ802 cloned into pNZ123; Cm$^r$ | This invention |

Abi$^+$, active abortive infection mechanism; Ap$^r$, ampicillin resistance; Cm$^r$, chloramphenicol resistance; Cm$^s$, sensitive to chloramphenicol; Em$^r$, erythromycin resistance; Tc$^r$, tetracycline resistance; Tc$^s$, sensitive to tetracycline; R$^+$/M$^+$, active restriction/modification enzymes.

Bacteriophages c2, p2, sk1, and jj50 were a gift from T. R. Klaenhammer (North Carolina State University). All phages were isolated from a single plaque with a 1-ml sterile pipette (Moineau, S., et al., Appl. Environ. Microbiol. 60:1832–1841 (1994)). They were transferred to GM17 containing 10 mM CaCl$_2$ previously inoculated (1%) with an overnight culture of the host strain. They were incubated at 30° C. until lysis and filtered through a 0.45 μm filter (Acrodics, Gelman Sciences, Ann Arbor, Mich.). High phage titers were then obtained by the method of Jarvis (Jarvis, A. W., Appl. Environ. Microbiol. 36:785–789 (1978)). Efficiency of plaquing (EOP) and adsorption assays were performed as described by Sanders and Klaenhammer (Sanders, M. E., et al., Appl. Environ. Microbiol. 40:500–506 (1980)). Cell survival was assayed by the method of Behnke and Malke (Behnke, D., et al., Virology, 85:118–128 (1978)) using a MOI of 3. One-step growth curves, center of infection (COI) assays, burst size and latent period determination were performed as described previously (Moineau, S., et al., Appl. Environ. Microbiol. 59:208–212 (1993)). The efficiency at which COI formed (ECOI) was obtained by dividing the number of COI from the resistant strain by the number of COI from the sensitive strain. The intracellular replication of φul36 DNA was also followed at time intervals after phage infection using the Hill et al. procedure (Hill, C., et al., Appl. Environ. Microbiol. 57:283–288 (1991)). The production of φul36 major capsid protein (MCP) was followed at time intervals after phage infection using monoclonal antibodies and a sandwich enzyme-linked immunosorbent assay (ELISA) as described previously (Moineau, S., et al., Appl. Environ. Microbiol. 59:2034–2040 (1993); and Moineau, S., et al., Appl. Environ. Microbiol. 59:208–212 (1993)).

DNA Isolation and Manipulation

Plasmid DNA from *E. coli* was isolated as described previously (Moineau, S., et al., Appl. Environ. Microbiol. 60:1832–1841 (1994)). Large quantities of *E. coli* plasmid DNA were isolated with the QIAGEN (Chatsworth, Calif.) plasmid MIDI or MAXI kit. Plasmid DNA from *L. lactis* was isolated using the method of O'Sullivan and Klaenhammer (O'Sullivan, D. J., et al., Appl. Environ. Microbiol. 59:2730–2733 (1993)). Large quantities of lactococcal plasmid DNA were obtained as described by Gonzalez and Kunka (Gonzalez, C. F., et al., Appl. Environ. Microbiol. 46:81–89 (1983)). Restriction endonucleases (Gibco/BRL, Grand Island, N.Y.) and T4 DNA ligase (Boehringer Mannheim, Indianapolis, Ind.) were used as described by the manufacturer's instructions.

Electroporation

*E. coli* was electroporated as previously described (Moineau, S., et al., Appl. Environ. Microbiol. 60:1832–1841 (1994)). *L. lactis* was grown in GM17 supplemented with 0.5M sucrose and 1% glycine and electroporated according to the Holo and Nes procedure (Holo, H., et al., Appl. Environ. Microbiol. 55:3119–3123 (1989)) as modified previously (Moineau, S., et al., Appl. Environ. Microbiol. 60:1832–1841 (1994)).

Sequencing

Figure 3:
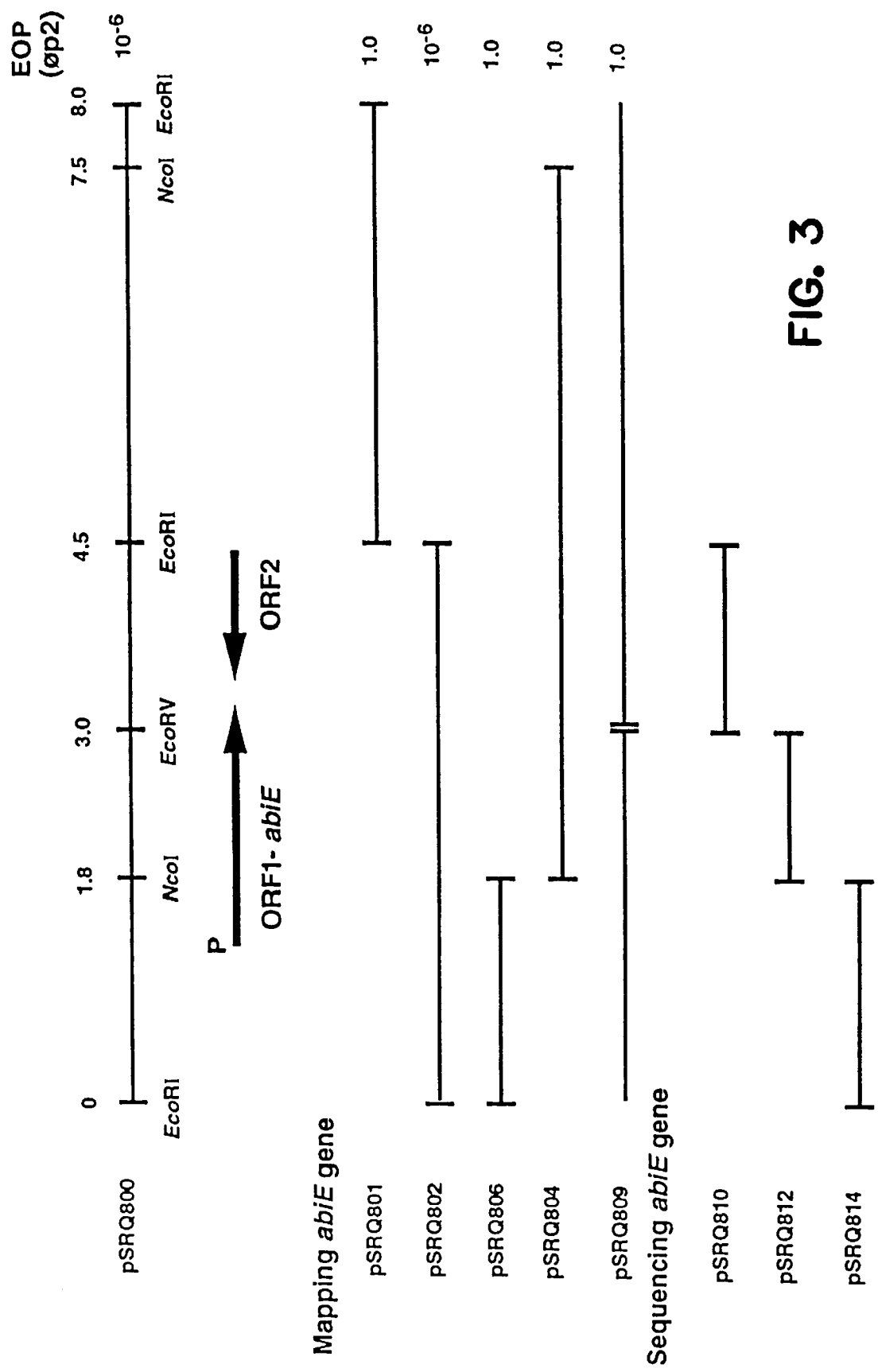
FIG. 3 is a linear restriction map of plasmid pSRQ800 and subclones used to localized the abiE gene. The DNA regions represented by the horizontal lines were subcloned into pSA3. The lines are bordered with vertical bars which indicates the site of cloning. The clones were electroporated in *L. lactis* LM0230 and the transformants tested for resistance against φp2. For sequencing purposes, the 4.5-kb EcoRI fragment was cut in three segments and subcloned into pBS.

The entire abi gene (4.5-kb EcoRI fragment from pSRQ800) could not be cloned in *E. coli* pBluescript KS+. The 4.5-kb insert was segmented into 3 small fragments (FIG. 3), subcloned into pBS and transformed into *E. coli* DH5α with blue and white color selection using IPTG (isopropyl-β-D-thiogalactopyranoside) and X-Gal (5-bromo-4-chloro-3-indoly-β-D-galactopyranoside). The resulting clones were named pSRQ810, pSRQ812 and pSRQ814 (FIG. 3). Nested deletions were made in both orientation from pSRQ810, pSRQ812 and pSRQ814 with an ERASE-A-BASE kit (Promega, Madison, Wis.). Plasmid DNA was extracted from the nested clones with QIAGEN and used directly for sequencing. The sequencing reactions were performed with the DYEDEOXY TERMINATOR TAQ sequencing kit for use on the model 373A automated DNA sequencing system (Applied Biosystems, Foster City, Calif.). The T7 and T3 primers were used for annealing.

DNA and Protein Analysis

The DNA sequence was analyzed with the Genetics Computer Group (Madison, Wis.) sequence analysis software. The GenBank (release 90, Aug. 15, 1995) and SwissProt (release 31.0 March 1995) databases were searched for homology with the deduced abiE gene and protein.

Nucleotide Sequence Accession Number

The complete sequence of 4,467 bp was deposited in the GenBank database and is available under the accession number U35629.

Results

Isolation of pSRQ800

The objective of this study was to identify phage resistance mechanism(s) present in *Lactococcus lactis* subsp. *lactis* W1. The total plasmid DNA of W1 was co-electroporated with the shuttle vector pSA3 into the laboratory strain *L. lactis* LM0230 which is phage-sensitive and plasmid-free. LM0230 was used because of its sensitivity to phages of the 936 and c2 species. The W1/pSA3 DNA ratio used for electroporation was 10:1. Erythromycin-resistant colonies were obtained (due to pSA3) and tested for phage resistance by spot assay ($10^4$φp2/spot). Some phage-resistant transformants were obtained, analyzed and found to contain pSA3 and a 8.0-kb plasmid which was named pSRQ800 (FIG. 1). One phage-resistant transformant was selected and named *L. lactis* SMQ-20.

Effectiveness of pSRQ800 on Three Lactococcal Phage Species

L. lactis SMQ-20 was tested for resistance against three small isometric-headed phages of the 936 species as well as three prolate-headed phages of the c2 species (Table 1). These 6 phages were individually tested on SMQ-20 and their EOPs are presented in Table 3. EOPs ranging from $10^{-6}$ to $10^{-7}$ were obtained for the 936-type phages φp2, φsk1 and φjj50 whereas EOPs of $10^{-1}$ were obtained with prolate φc2, φml3 and φeb1 (Table 3).

TABLE 3

EOPs of lactococcal phages at 30° C. on
Lactococcus lactis strains harboring pSRQ800.

| Phage | EOP |
|---|---|
| 936 species[a] | |
| φp2 | $4.6 \times 10^{-6}$ |
| φsk1 | $7.5 \times 10^{-7}$ |
| φjj50 | $6.0 \times 10^{-6}$ |
| c2 species[a] | |
| φc2 | $2.3 \times 10^{-1}$ |
| φml3 | $3.3 \times 10^{-1}$ |
| φeb1 | $2.7 \times 10^{-1}$ |
| p335 species[b] | |
| φul36 | $3.2 \times 10^{-6}$ |
| φQ30 | $3.0 \times 10^{-5}$ |
| φQ33 | $2.7 \times 10^{-8}$ |

[a]The EOP of the 936 and c2 phages was tested on L. lactis SMQ-20. The EOP of these phages is 1.0 on L. lactis LM0230.
[b]The EOP of the P335 phages was tested on L. lactis SMQ-88. The EOP of these phages is 1.0 on L. lactis SMQ-86.

The activity of pSRQ800 was also tested against P335 phages. Since LM0230 cannot replicate P335 phages, pSRQ800 was introduced into an appropriate host. L. lactis UL8 was electroporated with pSRQ802, a derivative of pSRQ800 (see below), and the transformant named SMQ-88. The EOPs of three P335 phages (φul36, φQ30 and φQ33) on SMQ-88 are presented in Table 3. The EOPs were variable ranging from $10^{-5}$ to $10^{-8}$. These results showed that the phage resistance mechanism encoded on pSRQ800 was effective against small isometric phages of the 936 and P335 species. However, PSRQ800 had very limited effect on prolate phages (c2 species).

Effect of Temperature on pSRQ800

The effect of temperature on the activity of pSRQ800 was tested using φp2. Similar EOPs were obtained at 21° C. and at 30° C. However, the EOP of φp2 increased from $4.6 \times 10^{-6}$ to $6.7 \times 10^{-2}$ at 38° C. indicating that the phage mechanism encoded on pSRQ800 is heat-sensitive.

Identification of the Phage Resistance Mechanism on pSRQ800

The type of phage defense mechanism located on pSRQ800 was examined. Adsorption experiments indicated that phages adsorbed to the same level (approximately between 90 to 95%) on the phage-sensitive L. lactis LM0230 and on the phage-resistant L. lactis SMQ-20, ruling out the adsorption blocking mechanism.

To determine if the mechanism was a R/M system, L. lactis SMQ-20 was challenged with high concentration of φp2. Phages capable of overcoming the pSRQ800 defense system and forming plaques on SMQ-20 were isolated. When these phages were tested back on SMQ-20, we observed that some phages were still inhibited by pSRQ800 while others were unaffected. These former phages were still untouched by pSRQ800 even after propagation on the sensitive host LM0230, indicating a permanent modification. These mutants or φp2 derivatives are under investigation. Nevertheless, these results ruled out the presence of host-controlled modifications such as R/M systems.

Based on the current classification of lactococcal phage resistance mechanisms, this system was considered an abortive infection mechanism. Furthermore when challenged with phages, L.lactis SMQ-20 exhibited the typical Abi[+] phenotype of reduced plaque size.

Localization of the Abi Gene on pSRQ800

Figure 2:
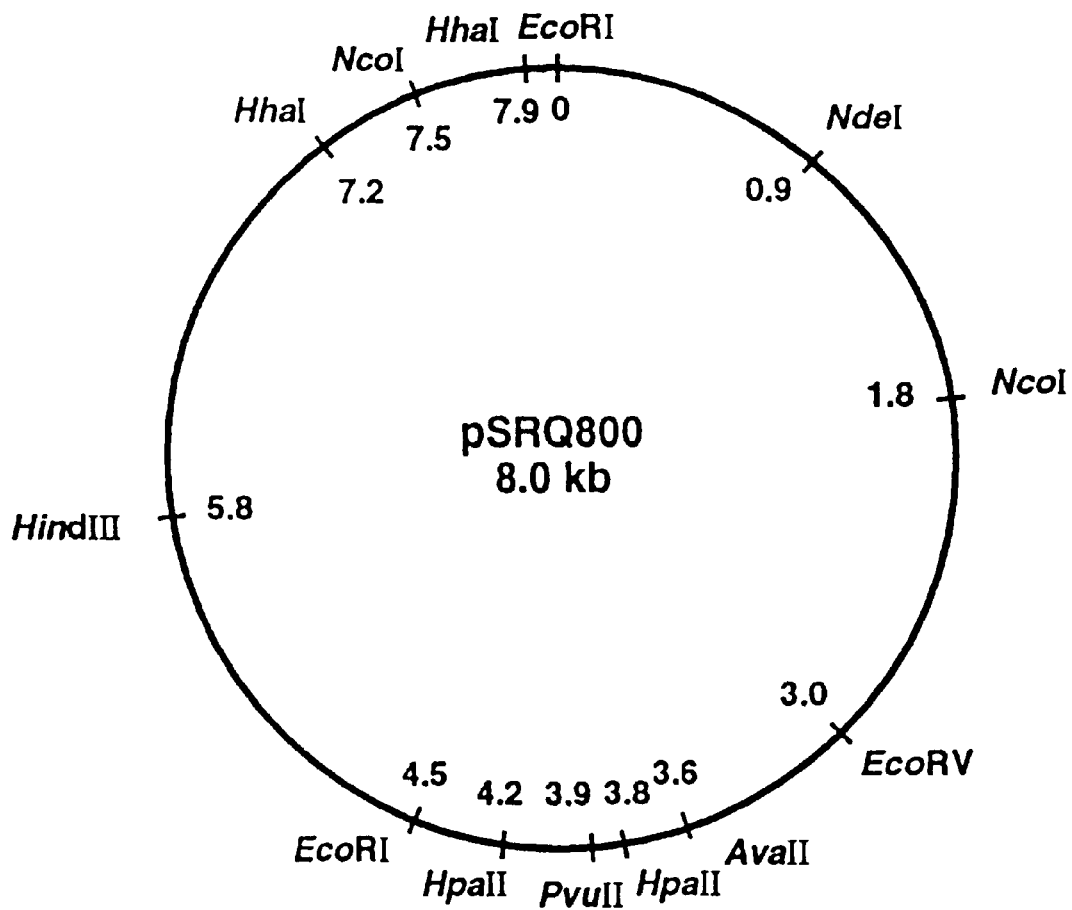
FIG. 2 is a circular restriction map of lactococcal plasmid pSRQ800. Site positions are indicated in kilobases.

The plasmid pSRQ800 was mapped using single, double and triple endonuclease digestions. The results are presented in FIG. 2. The following endonucleases did not cut pSRQ800: ApaI, AvaI, BalI, BamHI, HpaI, NruI, PstI, SalI, ScaI, SmaI, SphI, SstI, XbaI, XhoI. Since appropriate restriction sites were present on pSA3 and pSRQ800, total plasmid DNA from L. lactis SMQ-20 was digested with EcoRI, EcoRV and/or NcoI, and religated. The ligation mixture was directly electroporated in E. coli DH5α. After obtaining the appropriate clones, plasmid DNA was electroporated into L. lactis LM0230. The Em[r] transformants were tested for phage resistance. The relevant clones are presented in FIG. 3. Most of the clones (pSRQ801, pSRQ804, pSRQ806, pSRQ809) conferred no resistance (EOP of 1.0) against φp2 (FIG. 3). Only the clone pSRQ802 gave phage resistance similar to pSRQ800 (EOP of $10^{-6}$, FIG. 3). Thus, the full Abi[+] phenotype was localized on a 4.5-kb EcoRI fragment.

DNA and Protein Sequence Analysis of the Abi System

The 4.5-kb fragment containing the Abi[+] phenotype was sequenced in both directions and found to contain 4,467 bp (FIGS. 4A to 4D). This fragment had a G+C content of 29.5%. Two significant open reading frames (ORFs) were found on the 4.5-kb fragment. The first ORF was localized in one direction from position 1279 to 3075. The second ORF was localized in the other direction from position 4345 to 3491. The clones pSRQ804 and pSRQ809 which contained the full ORF2 but a disrupted ORF1 exhibited no resistance (EOP of 1.0) against φp2 (FIG. 3). We concluded that only ORF1 had all the necessary information to confer the Abi[+] phenotype.

The complete abi gene contained 1,797 bp with a very low GC content of 23.9%. A putative ribosome binding site (AAAGGAG) was found 8 bases preceding the abi gene start codon (FIGS. 4A to 4D). Putative promoter regions −10 (TATAAT), 16 bp spacer and −35 (AGCACA), were found upstream of the abi gene (FIGS. 4A to 4D). No region of dyad symmetry was found at the end of the abi gene suggesting the presence of a rho-dependent terminator. No significant DNA homology was found between this abi gene and the GenBank database including the previous sequenced L. lactis abi genes. This novel system was named AbiE.

The predicted AbiE protein contained 599 amino acids with an estimated weight of 71,416 Da and a pI of 8.0. No homology to the AbiE protein was found in the SwissProt database, confirming the novelty of AbiE. No transmembrane helix or secretory signals were found indicating that the AbiE protein is most likely intracellular. The Abi[+] phenotype was totally abolished with the clone pSRQ809 where the last 42 amino acids were missing from the AbiE protein. This result indicated that the C-terminal of the AbiE protein was critical to the Abi[+] phenotype.

Enhancement of AbiE Efficiency

The copy number of pSRQ800 was not determined but was estimated to be roughly the same as the low copy vector pSA3 (FIG. 1). The AbiE system was cloned into the high copy plasmid pNZ123 to determine the effect of gene copy number on the AbiE[+] phenotype. Previously, it was estimated that pSA3 was present in 5 to 10 copies (Dinsmore, P. K., et al., Appl. Environ. Microbiol. 60:1129–1136 (1994)) whereas pNZ123 was found between 50 to 100 copies in L. lactis (DeVos, W. M., FEMS Microbiol. Rev. 46:281–295 (1987)). The resulting high copy clone and transformant were named pSRQ815 and SMQ-143, respectively. The EOP of φp2 on SMQ-143 was $10^{-8}$ which is 2 negative logs higher than the EOP on SMQ-20 which contained the natural plasmid pSRQ800. Interestingly, the EOP of prolate phage c2 was also significantly decreased on SMQ-143. An EOP of $10^{-4}$ was observed with pSRQ815 whereas EOPs of $10^{-1}$ were observed with pSRQ800 and pSRQ802 (Table 4).

TABLE 4

EOP of φp2 and φc2 on *Lactococcus lactis* strains harboring various phage resistance mechanisms.

| Strains | EOP of φp2 | EOP of φc2 |
|---|---|---|
| LM0230 | 1.0 | 1.0 |
| SMQ-16 (pSA3) | 1.0 | 1.0 |
| SMQ-20 (pSA3 + pSRQ800) | $4.6 \times 10^{-6}$ | $2.3 \times 10^{-1}$ |
| SMQ-38 (pSRQ802) | $2.6 \times 10^{-6}$ | $6.9 \times 10^{-1}$ |
| SMQ-251 (pMIG3) | 1.0 | 1.0 |
| SMQ-130 (pSRQ813) | $1.8 \times 10^{-5}$ | 1.0 |
| SMQ-252 (pNZ123) | 1.0 | 1.0 |
| SMQ-143 (pSRQ815) | $3.8 \times 10^{-8}$ | $1.4 \times 10^{-4}$ |
| SMQ-39 (pSRQ701) | $1.9 \times 10^{-6}$ | $1.7 \times 10^{-4}$ |
| SMQ-138 (pSRQ701 + pSRQ813) | $<10^{-9}$ | $1.1 \times 10^{-4}$ |

These results indicated that multiple copies of abiE gene increase phage resistance against small isometric and prolate phages.

EXAMPLE 2

Another way of increasing the efficiency of Abi system is to supply in trans an another phage resistance mechanism (Sing, W. D., et al., Appl. Environ. Microbiol. 59:365–372 (1993)). Previously, we have isolated a L. lactis R/M system named LlaDCHI (formerly LlaII), that was encoded on the plasmid pSRQ700 (Moineau, S., et al., Appl. Environ. Microbiol. 61:2193–2202 (1995)). This plasmid was isolated from the industrial strain L. lactis subsp. cremoris DCH-4. The LlaDCHI genes were previously cloned into pSA3 and the Em$^r$ clone named pSRQ701 (Moineau, S., et al., Appl. Environ. Microbiol. 61:2193–2202 (1995)). Phage p2 had an EOP of $10^{-6}$ on L. lactis LM0230 harboring pSRQ701 (SMQ-39, Table 4). This phage had also an EOP of $10^{-6}$ on L. lactis LM0230 harboring pSRQ800 (SMQ-20, Table 4). The abiE gene was cloned into the vector pMIG3 (which contains a Cm$^r$ gene) and the clone was named pSRQ813. The EOP of φp2 on LM0230 containing pSRQ813 was slightly lower ($10^{-5}$) (SMQ-130, Table 4). Plasmids pSRQ701 and pSRQ813 were electroporated into L. lactis LM0230 and the resulting Em$^r$/Cm$^r$ transformant was named SMQ-138. The EOP of φp2 on SMQ-138 was $<10^{-9}$ indicating a full phage resistance phenotype. The EOP of the P335 phage ul36 was also $<10^{-9}$ on another L. lactis strain harboring both plasmids (data not shown). These results showed that AbiE and LlaDCHI R/M system, when supplied in trans, can complement each other to enhance phage resistance levels.

Intracellular Effects of AbiE System on the Phage Life Cycle

The effects of the AbiE system was tested on the phage ul36 life cycle using the phage-sensitive L. lactis SMQ-86 (pSA3) and phage-resistant L. lactis SMQ-88 (pSRQ802). Phage ul36 was selected because it was previously used to characterize two other Abi systems, AbiA and AbiC (Moineau, S., et al., Appl. Environ. Microbiol. 59:208–212 (1993)). The replication of φul36 was severely inhibited on SMQ-88 as seen by the EOP of $10^{-6}$ (Table 5 and FIG. 5C). Plaques were reduced in size from 1 mm to pinpoint and difficult to enumerate (data not shown). The average number of surviving cells following phage infection (MOI of 3) was 0.06% on SMQ-86 and 2.65% on SMQ-88 (Table 5).

TABLE 5

Specific effects of AbiE on the lactococcal phage ul36.

| Assays | SMQ-86 | SMQ-88 |
|---|---|---|
| EOP$^a$ | 1.0 | $3.15 \pm 1.63 \times 10^{-6}$ |
| Cell survival$^a$ (%) | $5.76 \pm 5.81 \times 10^{-2}$ | $2.65 \pm 0.85$ |
| ECOI$^b$ | 1.0 | $5.13 \pm 3.57 \times 10^{-3}$ |
| Burst size$^a$ | $504 \pm 164$ | $36 \pm 27$ |
| Latent period$^a$ (min) | 75 | 90 |
| DNA replication | +++ | − |
| MCP production$^a$ (%) | 100 | 1 |

$^a$Average of five trials.
$^b$Average of ten trials.

AbiE improved cell survival by approximately 50 fold but still a majority of infected cells died.

The ECOI for φul36 on SMQ-88 was 0.0051 indicating that only 5 out of 1000 infected cells successfully release viable phages (Table 5). The burst size of these productive infections was also reduced from an average of 504 phages on the phage-sensitive SMQ-86 to 36 phages on SMQ-88 (Table 5). Furthermore, the phage latent period was longer on SMQ-88 by approximately 15 min. (FIG. 5C). These results indicated that φul36 took more time to complete its life cycle on an AbiE$^+$ host and that the number of released phages was reduced by almost 15 fold. The cumulative effects of AbiE on the cell survival, ECOI, burst size and latent period were responsible for the severely reduced EOP of φul36 on SMQ-88 (Table 5).

The intracellular replication of φul36 DNA was followed on SMQ-86 and SMQ-88 (FIG. 5A and 5B). No replication of φul36 could be detected in L. lactis SMQ-88 whereas significant replication occurred in SMQ-86. The intracellular production of φul36 major capsid protein was also followed on SMQ-86 and SMQ-88 (FIG. 5C). The MCP is the most abundant structural protein of φul36 (Moineau, S., et al., Appl. Environ. Microbiol. 59:2034–2040 (1993)). Using an ELISA detection system, barely no MCP protein was detected in infected SMQ-88 cells (O.D.=0.389) whereas massive amount of MCP was detected in infected SMQ-86 cells (corrected O.D.=22.618). These results indicated that AbiE might act at or prior to phage DNA replication.

Results

As can be seen from Examples 1 and 2, *Lactococcus lactis* subsp. *blactis* strain W1 harbors a 8.0-kb plasmid (pSRQ800) coding for a temperature-sensitive abortive phage infection mechanism. The genetic element responsible for the Abi$^+$ phenotype was cloned and sequenced from pSRQ800. One gene was necessary for the Abi$^+$ phenotype.

AbiE displayed the classical abortive infection phenotype (Molineux, I. J., New Biol. 3:230–236 (1991); Sing, W. D., et al., J. Dairy Sci. 73:2239–2251 (1990); and Snyder, L., Mol. Microbiol. 15:415–420 (1995)). The presence of pSRQ800 increased the survival of infected cells by almost 50-fold demonstrating that AbiE was successful in aborting phage infection. Substantial cell death (98%) still occurred upon phage abortion (Table 5) suggesting that cell damage was too considerable for recovery. Very few infected AbiE$^+$ cells released progeny phages (0.5%) and when these rare productive infections occurred, the latent period was longer (by 15 min) and the burst size reduced by 15-fold. The overall effect of AbiE can be visualized as a reduction in number and size of phage plaques. Thus, AbiE acted internally to interfere with the phage lytic development.

AbiE encoded on its natural plasmid pSRQ800, inhibited the development of small isometric phages of the 936 and P335 species but had very limited effect on the prolate c2 species (Table 3). However if the abiE gene was cloned into the high copy vector pNZ123, a 4 log increase in resistance was noticed against phage φc2. This indicated that AbiE can be efficient against prolate phages when present in high copy number. A 2 log increase was also observed with φp2 (Table 3). Elevated efficiencies with high copy genes has also been observed with *L. lactis* AbiA (Casey, J., et al., Appl. Environ. Microbiol. 58:3283–3291 (1992); and Dinsmore, P. K., et al., Appl. Environ. Microbiol. 60:1129–1136 (1994)). Therefore, the natural plasmid pSRQ800 can bestow strong resistance against small isometric phages (936 and P335 species) and if the functional gene is delivered in an appropriate vector, AbiE can be effective against all three common lactococcal phage species (Jarvis, A. W., et al., Intervirology 32:2–9 (1991)).

Five other *L. lactis* Abi systems have been sequenced (Anba, J., et al., J. Bacteriol. 177:3818–3823 (1995); Cluzel, P. J., et al., Appl. Environ. Microbiol. 57:3547–3551 (1991); Durmaz, E., et al., J. Bacteriol. 174:7463–7469 (1992); Appl. C., et al., Appl. Environ. Microbiol. 56:2255–2258 (1990); and McLandsborough, L. A., et al., Appl. Environ. Microbiol. 61:2023–2026 (1995)). In all cases, only one gene was necessary to confer the Abi$^+$ phenotype. The five deduced Abi proteins had 628 (AbiA), 251 (AbiB), 344 (AbiC), 366 (AbiD), and 351 (AbiDl) amino acids. Thus, AbiE (599 aa, 71.4-kDa) would be closer to AbiA (628 aa and 73.8 kDa) based on protein size.

Functionally, AbiE was also similar to AbiA. This was evidenced by its efficient inhibition of 936 and P335 species (Casey, J., et al., Appl. Environ. Microbiol. 58:3283–3291 (1992); Dinsmore, P. K., et al., Appl. Environ. Microbial. 60:1129–1136 (1994); and Hill, C., et al., Appl. Environ. Microbiol. 56:2255–2258 (1990)), its increased activity against prolate phages with high copy (Casey, J., et al., Appl. Environ. Microbiol. 58:3283–3291 (1992); and Dinsmore, P. K., et al., Appl. Environ. Microbiol. 60:1129–1136 (1994)) and is heat sensitivity (Hill, C., et al., Appl. Environ. Microbiol. 56:2255–2258 (1990)). The AbiA phage target is currently unknown but it is believed to act prior to φ DNA replication since no DNA replication and MCP production were observed in infected AbiA$^+$ cells (Moineau, S., et al., Appl. Environ. Microbiol. 59:208–212 (1993)). Similar DNA replication and MCP production results were obtained with AbiE (FIGS. 5C and 5D). Even though AbiE shared phenotypic similarities with AbiA, no significant amino acid homology was found between the two proteins.

When developing phage-resistant cultures, one approach is to stack different phage resistance mechanisms within one strain (Durmaz, E., et al., Appl. Environ. Microbiol. 61:1266–1273 (1995); and Sing, W. D., et al., Appl. Environ. Microbiol. 59:365–372 (1993)). In fact some natural *L. lactis* plasmids like pTR2030 (Hill, C., et al., Appl. Environ. Microbiol. 56:2255–2258 (1990); and O'Sullivan, D. J., et al., J. Bacteriol. 177:134–143 (1995)) and pTN20 (Durmaz, E., et al., J. Bacteriol. 174:7463–7469 (1992)), already encode two distinct phage resistance mechanisms: an abortive infection mechanism and a R/M system. In these two plasmids, the Abi and R/M systems naturally complement each other to confer very strong phage resistance (EOP <$10^{-9}$). AbiE and LlaDCHI are considered strong phage resistance mechanisms since EOPs of $10^{-6}$ were observed with some phages (Moineau, S., et al., Appl. Environ. Microbiol. 61:2193–2202 (1995), Table 3). However on their own, both systems are leaky and a high phage population (>$10^6$) can overpower them. When AbiE and LlaDCHI were introduced in *L. lactis* strains, a full resistance phenotype (EOP <$10^{-9}$) was observed against 936 and P335 phages (Table 4). These results demonstrated the beneficial effect of providing in trans an Abi and a R/M system. Similar added resistance have been previously observed with other in trans *L. lactis* anti-phage systems (Durmaz, E., et al., Appl. Environ. Microbiol. 61:1266–1273 (1995); and Sing, W. D., et al., Appl. Environ. Microbiol. 59:365–372 (1993)). This is believed to be the first instance where such a strong resistance is observed with completely characterized Abi and R/M systems presented in trans in *L. lactis*.

From a practical and current regulatory point of view, the introduction of the natural plasmid pSRQ800 into an industrial *L. lactis* strain to confer strong resistance against small-isometric phages of the 936 and P335 species, is useful. It is useful against c2 phage species when the AbiE gene is provided in large copy number.

The foregoing description is only illustrative of the present invention and the present invention is limited only by the hereinafter appended claims.

We claim:

1. In a method for fermenting a dairy product, the improvement which comprises using a culture of *Lactococcus lactis* for the fermenting containing transferred DNA encoding a protein designated as AbiE and encoded by pSRQ800 which increases resistance to phages by aborting infection of *Lactococcus lactis* by the phages.

2. The method of claim 1 wherein the DNA is contained in strain *Lactococcus lactis* SMQ-20 deposited as NRRL-B-21443.

3. The method of claim 1 wherein the DNA is in a plasmid.

4. The method of claim 1 wherein the DNA is in a vector which was used to transfer the DNA by transformation.

5. The method of claim 1 wherein the DNA is in a shuttle vector pSA3.

6. The method of claim 1 wherein the DNA is in pNZ123.

7. The method of claim 1 wherein the DNA is in a recombinant plasmid containing DNA having a nucleotide sequence as set forth in SEQ ID NO 1 which encodes the protein designated as AbiE.

8. The method of claim 7 wherein the DNA is in a shuttle vector pSA3 containing the DNA.

9. The method of claim 7 wherein the DNA is in pNZ123 containing the DNA.

10. The method of claim 1 wherein the DNA is in a natural plasmid deposited as pSRQ800.

11. The method of claim 1 wherein, in addition, the culture contains DNA encoding a restriction or modification system which imparts phage resistance.

12. The method of claim 11 wherein the DNA is contained in *Lactococcus lactis* NRRL-B-21337.

* * * * *